United States Patent [19]

Doherty et al.

[11] Patent Number: 5,071,837

[45] Date of Patent: Dec. 10, 1991

[54] NOVEL RENIN INHIBITING PEPTIDES

[75] Inventors: Annette M. Doherty; Ila Sircar, both of Ann Arbor, Mich.

[73] Assignee: Warner-Lambert Company, Morris Plains, N.J.

[21] Appl. No.: 621,138

[22] Filed: Nov. 28, 1990

[51] Int. Cl.$^5$ .................. C07K 5/08; A61K 37/02
[52] U.S. Cl. ...................... 514/18; 530/331
[58] Field of Search ................ 514/18; 530/331

[56] References Cited

U.S. PATENT DOCUMENTS

| | | | |
|---|---|---|---|
| 4,479,941 | 10/1984 | Veber et al. | 424/177 |
| 4,855,303 | 8/1989 | Hoover et al. | 514/18 |
| 4,857,507 | 8/1989 | Rosenberg et al. | 514/18 |
| 4,882,420 | 11/1989 | Thaisrivongs | 530/330 |
| 4,985,407 | 1/1991 | Foxton et al. | 514/19 |

FOREIGN PATENT DOCUMENTS

| | | |
|---|---|---|
| 0222523 | 5/1987 | European Pat. Off. |
| 2171103 | 2/1986 | United Kingdom . |
| 2196958 | 8/1987 | United Kingdom . |
| 2203740 | 4/1988 | United Kingdom . |

OTHER PUBLICATIONS

Plattner et al., *J. Med. Chem.* 1988, 31(12):2277–2288.
Michael H. Gelb et al., "Fluoro Ketone Inhibitors of Hydrolytic Enzymes", Biochemistry, v. 24, No. 8, Apr. 9, 1985, pp. 1813 through 1817–M12.
U.S. Ser. No. 07/384,236 filed Jul. 24, 1989, which is a CIP of 07/206,023 filed Jun. 17, 1988, now abandoned, which is a CIP of 07/113,772 filed Oct. 26, 1987, now abandoned.

*Primary Examiner*—Lester L. Lee
*Assistant Examiner*—Stephen B. Maebius
*Attorney, Agent, or Firm*—Elizabeth M. Anderson

[57] ABSTRACT

The invention concerns certain orally active novel renin-inhibitory peptides which are useful for treating renin-associated hypertension, congestive heart failure, hyperaldosteronism, and glaucoma. It is also useful for treating diseases caused by retroviruses including HTLV-I, -II, and -III. Process for preparing the peptides, compositions containing them, and methods of using them are included. Also included is a diagnostic method which uses the compounds to determine the presence of renin-associated hypertension, congestive heart failure, or hyperaldosteronism.

9 Claims, No Drawings

NOVEL RENIN INHIBITING PEPTIDES

BACKGROUND OF THE INVENTION

Renin is a natural enzyme which is released into the blood from the kidney. It cleaves its natural substrate, angiotensinogen, releasing decapeptide, angiotensin I. This is in turn cleaved by converting enzyme in the lung, kidney, and other tissues to an octapeptide, angiotensin II. Angiotensin II raises blood pressure both directly by causing arteriolar construction and indirectly by stimulating release of the sodium-retaining hormone aldosterone from the adrenal gland causing a rise in extracellular fluid volume. Inhibitors of renin have been sought as agents for control of hypertension, congestive heart failure, and hyperaldosteronism.

The present invention concerns certain novel peptides which are selective for inhibition of renin versus related enzymes, especially cathepsin D and which possess potent oral activity. It also concerns pharmaceutical compositions containing these novel peptides, methods of treating renin-associated hypertension, congestive heart failure, hyperaldosteronism, and glaucoma as well as the use of the peptides as diagnostic tools. It also concerns a method for treating diseases caused by retroviruses including HTLV-I, -II, and -III. Methods for preparing the peptides are also disclosed.

U.S. Pat. No. 4,479,941 covers certain renin-inhibitory peptides of the formula

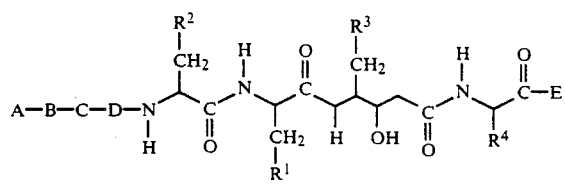

The compounds are useful as renin and acid protease inhibitors.

Since HIV protease, like renin, is an aspartyl protease, these compounds can also be used to treat diseases caused by retroviruses including HTLV-I, -II, and -III.

SUMMARY OF THE INVENTION

The present invention relates to novel peptides named

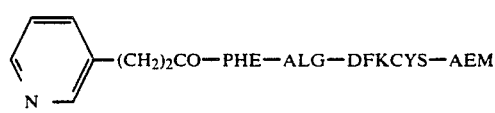

and

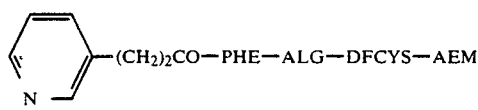

and the pharmaceutically acceptable salts thereof.

The invention also includes pharmaceutical compositions comprising an effective amount of an above peptide in admixture with a pharmaceutically acceptable carrier or excipient and a method for treating renin-associated hypertension in a patient suffering therefrom comprising administering to said patient the above pharmaceutical composition in unit dosage form.

Further, the invention includes a pharmaceutical composition comprising an effective amount of an above peptide in admixture with a pharmaceutically acceptable carrier or excipient, and a method for treating renin-associated hyperaldosteronism in a patient suffering therefrom comprising administering to said patient the above pharmaceutical composition in unit dosage form.

Further, the invention includes a pharmaceutical composition comprising an effective amount of an above peptide in admixture with a pharmaceutically acceptable carrier or excipient, and a method for treating renin-associated congestive heart failure in a patient suffering therefrom comprising administering to said patient the above pharmaceutical composition in unit dosage form.

Further, the invention includes a pharmaceutical composition comprising an effective amount of a peptide named above in admixture with a pharmaceutically acceptable carrier or excipient, and a method for treating diseases caused by retroviruses including HTLV-I, -II, and -III in a patient suffering therefrom comprising administering to said patient the above pharmaceutical composition in unit dosage form.

The present invention also includes the use of the above peptides as diagnostic tools for the identification of cases of hypertension due to renin excess.

The invention further includes methods for preparing the above peptides.

DETAILED DESCRIPTION

The following table provides a dictionary of the terms used in the description of the invention.

TABLE 1

| Abbreviated Designation | Amino Acid |
|---|---|
| PHE | L-Phenylalanine |
| DFKCYS | 4(S)-Amino-3-oxo-2,2-difluoro-5-cyclohexane pentanoic acid |
| DFCYS | 4(S)-Amino-3(R)-hydroxy-2,2-difluoro-5-cyclohexane pentanoic acid |
| ALG | 2(S)-Amino-4-pentenoic acid (Allylglycine) |
| | Amides With |
| AEM | 2-Aminoethylmorpholine |
| | —NHCH₂CH₂—N⌒O⌒ |
| | Solvents and Reagents |
| DMF | N,N-Dimethylformamide |
| DMSO | Dimethylsulfoxide |
| HOBT | 1-Hydroxybenzotriazole |
| DCC | N,N'-Dicyclohexylcarbodiimide |
| CH₂Cl₂ | Dichloromethane |

The compounds of the instant invention

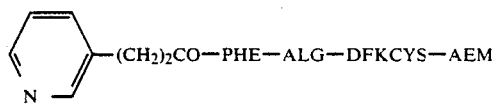

and

TABLE 1-continued

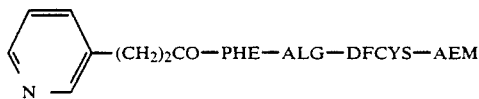
—(CH$_2$)$_2$CO—PHE—ALG—DFCYS—AEM and the pharmaceutically acceptable salts thereof are useful for treating renin-associated hypertension, congestive heart failure, and hyperaldosteronism. They are also useful as diagnostic tools for determining the presence of renin-associated hypertension or hyperaldosteronism. They are also expected to be useful for treating diseases caused by retroviruses including HTLV-I, -II, and -III.

The compounds of the present invention have the advantage of increased hydrophilicity relative to renin inhibitors known in the art. This property imparts good aqueous solubility which may facilitate absorption.

The compounds include solvates and hydrates and pharmaceutically acceptable acid addition salts of the compounds of the invention.

The term pharmaceutically acceptable acid addition salt is intended to mean a relatively nontoxic acid addition salt either from inorganic or organic acids such as, for example, hydrochloric, hydrobromic, hydroiodic, sulfuric, phosphoric, acetic, citric, oxalic, malonic, salicylic, malic, benzoic, gluconic, fumaric, succinic, ascorbic, maleic, tartaric, methanesulfonic, and the like. The salts are prepared by contacting the free base form with a sufficient amount of the desired acid to produce a salt in the conventional manner. The free base forms may be regenerated by treating the salt form with a base.

The modified peptides of the present invention possess one or more chiral centers and each center may exist in the R(D) and S(L) configuration. Unless otherwise specified, the L form is the preferred embodiment. The present invention includes all enantiomeric and epimeric forms as well as the appropriate mixtures thereof.

Some of the above novel peptides may be prepared in accord with well-known procedures for preparing peptides from their constituent amino acids. Other of the novel peptides of the present invention are prepared by a step-wise procedure or by a fragment coupling procedure depending upon the particular final product desired.

The strategy of peptides chain assembly and selection and removal of protecting groups is discussed in Chapter 1, "The Peptide Bond", in "The Peptides. Analysis, Synthesis, Biology," E. Gross and J. Meienhofer, Eds., Academic Press, New York, N.Y., 1979, pp. 42–44.

The DCC/HOBT method of coupling is well-known to those skilled in the art and is discussed in Chapter 5, "The Carbodiimide Method" by D. H. Rich and J. Singh in "The Peptides. Analysis, Synthesis, Biology," E. Gross and J. Meienhofer, Eds., Academic Press, New York, N.Y., 1979, pp. 42–44.

Peptide coupling depends on activating the carboxy terminus and condensing it with another peptide containing a free amino terminus. In addition to the DCC coupling method described above, other methods of activating the carboxyl group of a protected amino acid include:

1) The azide method—described in Chapter 4 of the above reference.

2) The mixed anhydride method—described in Chapter 6 of the above reference.

3) The active ester method—described in Chapter 3 of the above reference.

Pharmaceutical compositions which comprise an effective amount of the compound in combination with a pharmaceutically acceptable carrier are part of the present invention. An important aspect of the present invention is a method of treating renin-associated hypertension in a mammal which comprises administering a pharmaceutical composition containing an effective amount of a compound of the invention in combination with a pharmaceutically acceptable carrier to the mammal.

Another equally important aspect of the present invention is a method of treating renin-associated hyperaldosteronism in a mammal which comprises administering a pharmaceutical composition containing an effective amount of a compound of the invention in combination with a pharmaceutically acceptable carrier to the mammal.

An additional aspect of the present invention is a method for treating renin-associated congestive heart failure in a mammal which comprises administering a pharmaceutical composition containing an effective amount of a compound in combination with a pharmaceutically acceptable carrier to the mammal. The effectiveness of the aforementioned compounds is determined by a test for in vitro renin inhibitory activity. This activity is determined by a standard radioimmunoassay for angiotensin I. In this assay, the enzyme, renin, incubated for 2 hours at 37° in the presence of a substrate, angiotensinogen, generates the product, angiotensin I. Test compounds are added to the incubation mixture. Relative activity is reported as the IC$_{50}$, which is the molar concentration of test compound, causing a 50% inhibition of the renin activity.

TABLE 2

| Compound | IC$_{50}$ (nM) Monkey Renin | IC$_{50}$ Bovine Cathepsin D |
|---|---|---|
| Example 1 | $0.23 \times 10^{-9}$ | $0.16 \times 10^{-5}$ |
| Example 2 | $0.22 \times 10^{-9}$ | $1 \times 10^{-4}$ |

As can be seen from the above table, the compounds of the present invention have a significant effect on the activity of renin and thus are useful for the treatment of renin-associated hypertension, hyperaldosteronism, congestive heart failure, and glaucoma.

Compounds of this invention have also demonstrated in vivo activity represented by lowering blood pressure in conscious monkeys. In vivo effectiveness is determined by their effect on blood pressure in conscious, sodium-deplete, normotensive cynomolgus monkeys.

The following describes this test. Monkeys were acclimated to a low sodium diet and trained to rest quietly in a restraining device. Next, vascular access ports were surgically implanted for intravenous administration of test compounds and direct measurement of blood pressure. At least 1 week was allowed for recovery from surgery before sodium depletion was accomplished by giving furosemide (1 mg/kg/day, IM) for 4 consecutive days. On the seventh day, animals were removed from their home cage and placed in the restraining device. After a 20- to 30-minute acclimation period, a control blood sample (arterial) was taken for determination of plasma renin activity (PRA). Next, either vehicle (absolute ethanol, 0.21 mL/kg) or test compound (5 mg/kg) was infused intravenously over a 10-minute period.

Blood pressure was monitored continuously throughout the entire pre- and post-dose period. Blood sample were taken at the mid-point of the infusion and at 0, 15, 30, and 60 minutes post-infusion.

The compounds of the present invention also possess the advantage of increased selectivity toward the renin enzyme versus other aspartic proteinase enzymes, specifically cathepsin D, compared with many other fluorostatones containing other acyl groups at the $P_4$ position. This property is due to the novel combination of basic $P'_2$ and $P_4$ groups.

At an oral dose of 3 mg/kg, the compound produced a drop in mean blood pressure equivalent to 71% of the drop produced by a maximally effective intravenous dose of the angiotensin receptor antagonist saralasin (22 mm Hg absolute drop). In a second group of monkeys given 10 mg/kg, a blood pressure reduction equivalent to 92% of the saralasin effect was observed (23 mm Hg).

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powder and tablets preferably contain from 5 to 10 to about 70 percent of the active ingredient. Suitable solid carriers are magnesium carbonate, magnesium stearate, talc, sugar, tragacanth, methylcellulose, a low melting wax, cocoa butter, and the like. The term "preparation" is intended to include the formulation of the active compounds with encapsulating material as carrier providing a capsule in which the active component (with or without other carriers) is surrounded by carrier, which is thus in association with it. Similarly, cachets are included. Tablets, powders, cachets, and other capsules can be used as solid dosage forms suitable for oral administration.

The compound of the present invention may be administered orally, buccally, parenterally, by inhalation spray, rectally, or topically in dosage unit formulations containing conventional nontoxic pharmaceutically acceptable carriers, adjuvants, and vehicles as desired. The term parenteral as used herein includes subcutaneous injections, intravenous, intramuscular, intrasternal injection, or infusion techniques.

For preparing suppositories, a low melting wax such as a mixture of fatty acid glycerides or cocoa butter is first melted, and the active ingredient is dispersed homogeneously therein by stirring. The molten homogeneous mixture is then poured into convenient sized molds, allowed to cool, and thereby solidify.

Liquid form preparations include solutions, suspensions, and emulsions. As an example may be mentioned water or water/propylene glycol solutions for parenteral injection. Liquid preparations can also be formulated in solution in aqueous polyethyleneglycol solution. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted shortly before use to liquid form preparations for either oral or parenteral administration. Such liquid forms include solutions, suspensions, and emulsions. These particular solid form preparations are most conveniently provided in unit dosage form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like, as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably 5 to 100 mg according to the particular application and the potency of the active ingredient. The compositions can, if desired, also contain other compatible therapeutic agents.

In therapeutic use as renin inhibitors, the mammalian dosage range for a 70-kg subject is from 0.1 to 100 mg/kg of body weight per day optionally in divided portions. The dosages, however, may be varied depending upon the requirements of the patient, the severity of the condition being treated, and the compound being employed. Determination of the proper dosage for a particular situation is within the skill of the art. Generally, treatment is initiated with small dosages which are less than the optimum dose of the compound. Thereafter the dosage is increased by small increments until the optimum effect under the circumstances is reached. For convenience, the total daily dosage may be divided and administered in portions during the day if desired.

The following examples are provided to enable one skilled in the art to practice the present invention. These examples are not intended in any way to limit the scope of the invention but are illustrative thereof.

EXAMPLE 1

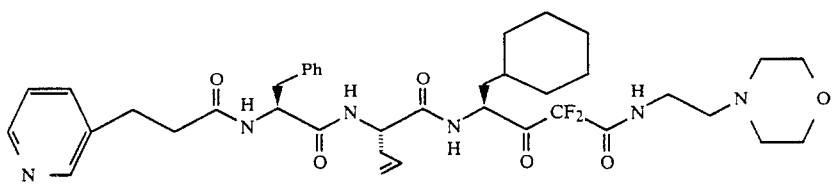

To a solution of the alcohol of Example 2 (2.95 g, 3.98 mmol) in dry CH$_2$Cl$_2$ (80 mL) at 0° C. was added dichloroacetic acid (0.83 mL, 10 mmol) followed by DMSO (8 mL) and DCC (8.20 g, 40 mmol). The mixture was stirred at 0° C. for 1 to 2 hours and then at room temperature overnight (18 hours). Oxalic acid (5.20 g) was dissolved in MeOH (12.5 mL) and this solution was added to the reaction. After about 20 minutes, the precipitated solid was filtered and the filtrate evaporated. The residue was diluted with ethyl acetate (400 mL) and the solution again filtered. Ethyl acetate solution was extracted with 20% aqueous H$_3$PO$_4$ (4×100 mL). The combined aqueous layers were washed once with ethyl acetate (100 mL). The aqueous solution was brought to ca pH 6 by slow addition of cold aqueous NH$_4$OH and extracted with several portions of ethyl acetate (4×200 mL). The organic layer was washed with brine, dried (Na$_2$SO$_4$), and the solvent was evaporated to afford an off-white foam (2.48 g). It was dissolved in ethanol (20 mL) and treated with methanesulphonic acid (0.32 g, 3.98 mmol). The solution was evaporated and dried for several hours under reduced pressure to afford the product (2.40 g, 81.5%) as an off-white foam. The structure was confirmed by NMR and mass spectroscopy. MS (FAB) 739.3 (m+1).

Calcd. for C$_{39}$H$_{52}$N$_6$O$_6$F$_2$·CH$_3$SO$_2$H·H$_2$O: C, 56.33; H, 6.86; N, 9.84; S, 3.75. Found: C, 56.82; H, 6.89; N, 9.16; S, 3.91.

EXAMPLE 2

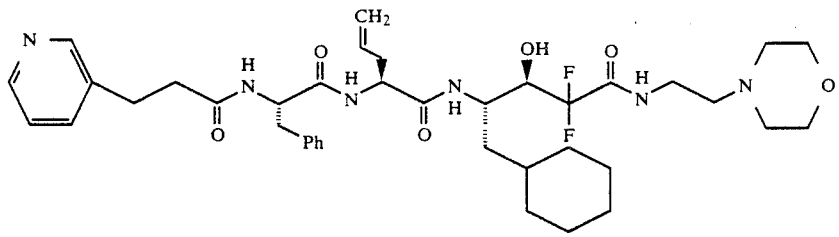

The acid 3-pyridylethylcarbonyl-PHE (1.78 g, 5.97 mmol) was suspended in dry CH$_2$Cl$_2$ (50 mL) followed by addition of HOBT (0.81 g, 5.97 mmol) and DMF (50 mL). The reaction mixture was cooled to 0° C. and after 30 minutes ALG-DFCYS-AEM (2.75 g, 5.97 mmol) in CH$_2$Cl$_2$ (50 mL) was added. After 30 minutes DCC (1.23 g, 6.0 mmol) was added and the reaction stirred at 0° C. for 1 hour followed by room temperature overnight (18 hours). The suspension was filtered and the precipitate washed with several portions of ethyl acetate/Et$_2$O. The filtrate was washed with saturated aqueous bicarbonate solution, dried (Na$_2$SO$_4$) and evaporated. The resulting yellow solid was washed well with ethyl acetate/Et$_2$O and combined with the first precipitate to afford the product (4.02 g, 90.5%). The structure was confirmed by NMR and mass spectroscopy, mp 195°–201° C. MS (FAB) 741.5 (m+1).

Calcd. for C$_{39}$H$_{52}$N$_6$O$_6$F$_2$: C, 63.23; H, 7.35; N, 11.34. Found: C, 63.46; H, 7.57; N, 11.34.

What is claimed is:

1. A compound

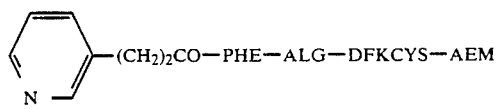

or a pharmaceutically acceptable salt thereof.

2. A compound

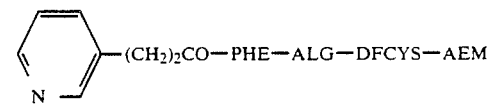

or a pharmaceutically acceptable salt thereof.

3. A pharmaceutical composition for treating hypertension comprising a renin-inhibitory effective amount of a peptide as claimed in claim 1 or claim 2 together with a pharmaceutically acceptable carrier.

4. A method of treating hypertension which comprises administering to a mammal a pharmaceutical composition as claimed in claim 3.

5. A pharmaceutical composition comprising a hyperaldosteronism-inhibitory effective amount of a peptide as claimed in claim 1 or claim 2 together with a pharmaceutically acceptable carrier.

6. A method of treating hyperaldosteronism which comprises administering to a mammal a pharmaceutical composition as claimed in claim 5.

7. A pharmaceutical composition comprising an amount effective for treating congestive heart failure of a peptide as claimed in claim 1 or claim 2 together with a pharmaceutically acceptable carrier.

8. A method of treating congestive heart failure which comprises administering to a mammal a pharmaceutical composition as claimed in claim 7.

9. A method of determining the presence of hypertension in a patient, comprising administering to such a patient, at a hypotensive dosage level and as a single dose, a peptide according to claim 1 or claim 2, followed by monitoring of said patient's blood pressure.

* * * * *